United States Patent
Seidling et al.

(10) Patent No.: US 8,691,301 B2
(45) Date of Patent: Apr. 8, 2014

(54) SURFACTANT GAS PRESSURIZED LIQUID COMPOSITION AND METHOD AND PACKAGE FOR DELIVERING

(75) Inventors: Jeffery Richard Seidling, Neenah, WI (US); Scott W. Wenzel, Neenah, WI (US); Stacy Averic Mundschau, Weyauwega, WI (US); David W. Koenig, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1258 days.

(21) Appl. No.: 12/217,070

(22) Filed: Jun. 30, 2008

(65) Prior Publication Data

US 2009/0324505 A1    Dec. 31, 2009

(51) Int. Cl.
*A61K 35/66* (2006.01)
*A61K 9/12* (2006.01)
*A61K 8/00* (2006.01)
*A01N 63/00* (2006.01)

(52) U.S. Cl.
USPC .............. 424/780; 424/43; 424/47; 424/93.4; 424/93.51

(58) Field of Classification Search
None
See application file for complete search history.

(56) References Cited

U.S. PATENT DOCUMENTS

| | | | | |
|---|---|---|---|---|
| 4,229,569 A | * | 10/1980 | Feldman et al. | 528/501 |
| 4,284,533 A | * | 8/1981 | Imamura et al. | 510/398 |
| 4,784,847 A | * | 11/1988 | Zulliger-Bopp et al. | 424/69 |
| 4,808,388 A | | 2/1989 | Beutler et al. | |
| 5,026,551 A | | 6/1991 | Yorozu et al. | |
| 5,034,226 A | * | 7/1991 | Beck | 424/401 |
| 5,527,892 A | | 6/1996 | Borsotti et al. | |

(Continued)

FOREIGN PATENT DOCUMENTS

| | | | | |
|---|---|---|---|---|
| CN | 88101028 A | | 8/1988 | |
| FR | 2825629 | * | 12/2002 | |
| JP | 2004-215634 A | * | 8/2004 | |
| SU | 1258904 A | * | 12/1987 | ............... A23L 2/00 |
| WO | WO 2003/059261 A2 | | 7/2003 | |
| WO | WO 2009/000570 | * | 12/2008 | |

OTHER PUBLICATIONS

Dharmadhikari. Compostition of Grapes. Retrieved from the internet. <http://www.extension.iastate.edu/NR/rdonlyres/A647BBD4-08D5-494B-A55B-680667E6C342/56373/compositionofgrapes.pdf>. Retrieved on Sep. 9, 2011. 6 pages.*

(Continued)

*Primary Examiner* — Chris R Tate
(74) *Attorney, Agent, or Firm* — Denise L. Stoker; R. Joseph Foster, III

(57) ABSTRACT

A self gassing composition comprising at least one surfactant and a fermentation base including a gas producing organism and at least one sugar is disclosed. Use of a nonionic surfactant in the self gassing composition allows the fermentation base to continue reacting and producing gas. Additionally, a personal care cleansing product and method for storing and delivering an aqueous composition having at least one surfactant and pressurized gas dissolved therein is disclosed. In one aspect, the composition is stored in an internal reservoir in a container such that when a sealing device is removed from a valveless opening, the composition foams and plumes out the opening of the container as the gas dissolved in the composition is released. In addition to the self gassing composition, a pressurized gas may be injected into a surfactant composition to produce the gas pressurized cleaning composition.

23 Claims, 1 Drawing Sheet

(56) References Cited

U.S. PATENT DOCUMENTS

Figure 2:
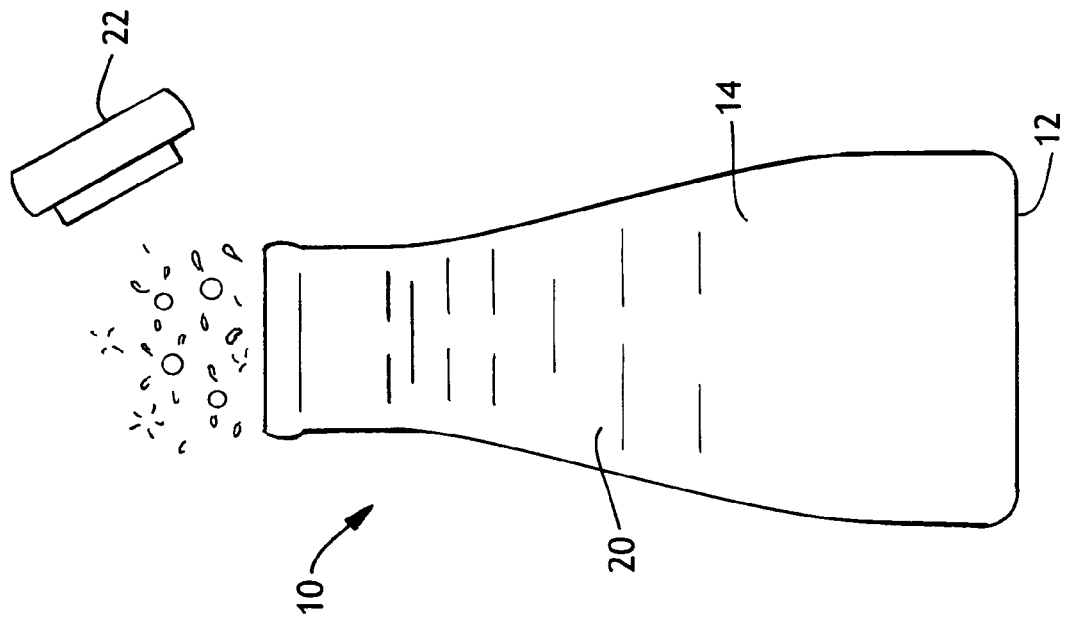

| | | | | |
|---|---|---|---|---|
| 5,627,134 | A | * | 5/1997 | O'Neal et al. ............... 504/130 |
| 5,770,543 | A | | 6/1998 | Garst et al. |
| 5,935,915 | A | * | 8/1999 | Gordon et al. ............... 510/130 |
| 6,033,887 | A | * | 3/2000 | Charpentier ................. 435/178 |
| 6,074,647 | A | | 6/2000 | Zimmerman et al. |
| 6,627,585 | B1 | | 9/2003 | Steer |
| 2001/0044393 | A1 | * | 11/2001 | Peterson et al. ............ 510/130 |
| 2004/0009143 | A1 | * | 1/2004 | Golz-Berner et al. ......... 424/74 |
| 2007/0292919 | A1 | | 12/2007 | Holt et al. |
| 2008/0248077 | A1 | * | 10/2008 | Gellert et al. ................ 424/422 |
| 2010/0215841 | A1 | * | 8/2010 | Thompson ................. 427/96.4 |
| 2011/0126364 | A1 | * | 6/2011 | Mishina et al. ................. 8/467 |
| 2011/0163469 | A1 | * | 7/2011 | Little et al. ...................... 264/9 |

OTHER PUBLICATIONS

Code of Federal Regulations, Title 21, Food and Drugs, Pt. 170-199. Revised as of Apr. 2005. IntraWEB, LLC, Jun. 2005. pp. 87-89.*

Internet document entitled "Wholesale Polyglycerol Oleate (Polyglycerol oleic acid, ester, Polyglyceryl Oleate)", 2 pages, downloaded on Jul. 10, 2013 from the website http://www.ebiochem.com/product/.*

Internet document entitled Johnson a Family Company—Our Ingredients from A to Z, Definition: Polyglyceryl oleate, 1 page, downloaded on Jul. 10, 2013 from the website http://www.whatsinsidescjohnson.com/en-us;ingredients/P/polyglyceryl-oleate.aspx.*

* cited by examiner

SURFACTANT GAS PRESSURIZED LIQUID COMPOSITION AND METHOD AND PACKAGE FOR DELIVERING

BACKGROUND

1. Field

The present disclosure relates to a method, a package for storing and delivering a surfactant composition, and self foaming or gas pressurized composition. More particularly, an aqueous composition having at least one surfactant and a fermentation base is disclosed. Additionally, a package is disclosed for providing and storing a surfactant gas pressurized liquid composition such that when a sealing device is removed from the package, the composition foams and plumes out the opening of the container.

2. General Background

The use of cleansing product dispensers such as liquid soaps and bubble baths is well known in the art. Some known liquid dispensers for dispensing liquids without foaming of the liquids are also known. Many of these containers include non-collapsible or rigid sealed containers that have the disadvantage of requiring various one-way valve mechanisms to permit gas to enter the containers under vacuum to equalize the pressure in the containers with atmospheric pressure. Such one-way valves typically suffer the disadvantage that they maintain at least some vacuum pressure differential in the container and with many viscous soaps, the presence of even a slight vacuum can negatively affect dispensing. Additionally, liquid soap dispensers heretofore devised and utilized are known to consist basically of familiar, expected and obvious structural configurations.

As a result, in the competitive marketplace of cosmetics it is often difficult for a consumer to differentiate between similar products, especially for bubble baths and body washes. Marketing of the product through packaging and ingredient choices is utilized to make a product stand out. However, there is nothing to differentiate the utilization of the product during use by a consumer. Thus, there is a need to provide a method of packaging and delivering a personal care cleansing product that will differentiate the product from other forms and provide a consumer with an improved experience in utilizing the product.

SUMMARY

In one aspect, a self gassing or carbonating aqueous composition containing a fermentation base and at least one surfactant is disclosed. The fermentation base includes at least one fermentable carbohydrate and a gas producing organism. Various sugars, including glucose, fructose and sucrose, may be utilized as the fermentable carbohydrate. In an exemplary aspect, the gas producing organism is yeast or ethanol producing bacteria producing carbon dioxide via ethanol fermentation.

In another aspect, the at least one surfactant in the gas pressurized liquid composition comprises at least one nonionic surfactant. Use of nonionic surfactants allows for a surfactant to be included in the composition while also not killing the gas producing organism. As a result, the pressurized gas in the composition may be produced in situ.

In an exemplary aspect, the composition is pressurized by fermenting a fruit juice and producing carbon dioxide in the aqueous composition. In this implementation, the surfactant included with the composition is a nonionic surfactant. Suitable nonionic surfactants include, for example, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_{6-22}$) alcohol, including 3 to 20 ethylene oxide moieties, polyoxyethylene-20 isohexadecyl ether, polyoxyethylene-23 glycerol laurate, PEG-80 sorbitan laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG-600 dioleate, PEG-400 dioleate, decyl glucoside, poloxamers such as poloxamer 188, polysorbate 21, polysorbate 40, polysorbate 60, polysorbate 61, polysorbate 65, polysorbate 80, polysorbate 81, polysorbate 85, sorbitan caprylate, sorbitan cocoate, sorbitan diisostearate, sorbitan dioleate, sorbitan distearate, sorbitan fatty acid ester, sorbitan isostearate, sorbitan laurate, sorbitan oleate, sorbitan palmitate, sorbitan sesquiisostearate, sorbitan sesquioleate, sorbitan sesquistearate, sorbitan stearate, sorbitan triisostearate, sorbitan trioleate, sorbitan tristearate, sorbitan undecylenate, PEG-10 Dimethicone, PEG-12 Dimethicone, PEG-14 Dimethicone, PEG-17 Dimethicone, PPG-12 Dimethicone, PPG-17 Dimethicone and derivatized/functionalized forms thereof such as Bis-PEG/PPG-20/20 Dimethicone Bis-PEG/PPG-16/16 PEG/PPG-16/16 Dimethicone, PEG/PPG-14/4 Dimethicone, PEG/PPG-20/20 Dimethicone, PEG/PPG-20/23 Dimethicone, Perfluorononylethyl Carboxydecyl PEG-10 Dimethicone and/or mixtures thereof.

In another aspect, a method and package for storing and delivering a gas pressurized liquid composition is disclosed. The method includes providing a valveless container having an opening and a sealing device and storing an aqueous composition under elevated pressure whereby removing the sealing device from the opening and allowing the composition to foam and plume out the opening of the container.

In exemplary aspects, a surfactant is present from about 0.01 wt. % to about 60 wt. %, and more preferably about 0.05 wt. % to about 50 wt. % based on the total weight of the liquid composition.

In another aspect, the product is prepared by injecting the aqueous composition with a gas and bottling the composition under high pressure. The gas may be selected from, for example, air, carbon dioxide, nitrogen, nitric oxide, isobutene, other suitable inert carriers, and other gases that will generate enough pressure in the container.

In another aspect, the injectable gas product includes at least one surfactant that is selected from anionic, nonionic, cationic, amphoteric, zwitterionic surfactants and mixtures thereof. In an exemplary aspect, the at least one surfactant is a mixture of amphoteric and anionic surfactant. The anionic surfactant may be sodium lauryl sulfate and the amphoteric surfactant may be cocamidopropyl betaine.

In another aspect, the product includes a sealing device that may be a pop-top utilized in aluminum cans, a cork utilized for stopping bottles and frangible seals. Preferably, the container provided is a bottle and the sealing device is a cork, or any material used as a bottle stopper.

In another aspect, the gas pressurized liquid composition further comprises an ingredient to promote an additional end benefit. These ingredients may be selected from emollients, humectants, natural fats and oils, anti-irritants, antimicrobial agents, antioxidants, anti-parasitic agents, antipuritics, antifungals, antiseptic actives, keratolytic actives, anti-stinging agents, anti-reddening agents, astringents, biological actives, deodorants, external analgesics, film formers, fragrances, skin condition agents, skin exfoliating agents, skin protectants, skin soothing ingredients, sunscreens and combinations thereof.

BRIEF DESCRIPTION

Figure 1:
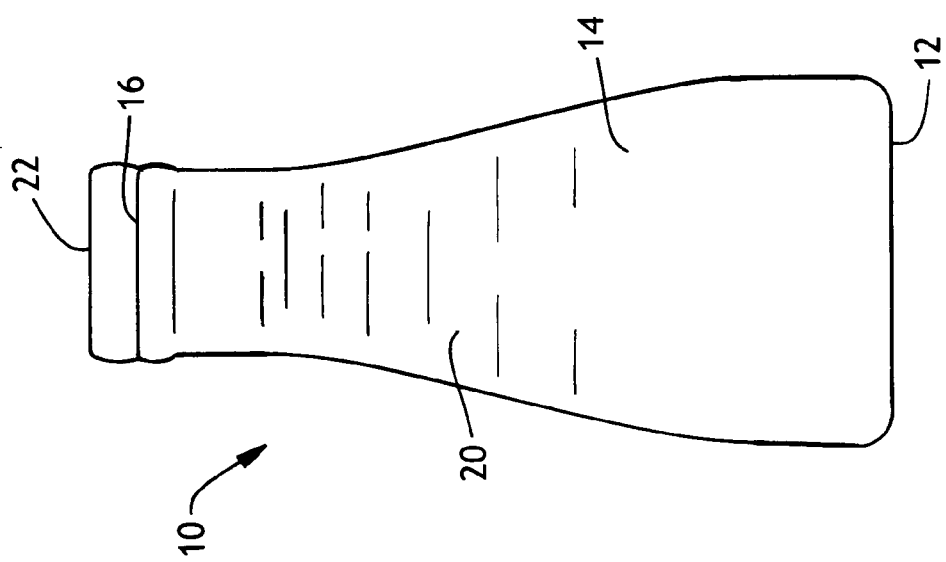

FIG. 1 illustrates an exemplary personal care product of the present disclosure; and FIG. 2 illustrates an exemplary personal care product of the present disclosure after the product has been opened.

DETAILED DESCRIPTION

Generally, a self foaming or gassing composition and package for storing and delivering a surfactant composition is disclosed. An exemplary aqueous composition comprises at least one surfactant wherein the aqueous composition is a gas pressurized liquid composition. As used herein, a gas pressurized liquid composition is a liquid composition having a gas dissolved therein. In exemplary implementations, the composition may be self carbonating or gassing. The gas pressurized liquid composition may be stored in an internal reservoir in a container such that when a sealing device is removed from the opening, the composition foams and plumes out the opening of the container as the gas dissolved in the composition is released.

The gas pressurized liquid composition of the present disclosure includes at least one surfactant. Surfactants, among other things, aid in the removal of dirt from skin. Suitable surfactants for the present disclosure are water soluble, able to tolerate acidic environments, and generate foam.

To produce a gas pressurized liquid composition, the aqueous composition may contain a fermentation base and at least one surfactant. The fermentation base may include at least one fermentable carbohydrate and a gas producing organism. In an exemplary aspect, ethanol fermentation is utilized to produce the fermentation base. Ethanol fermentation is the biological process by which sugars such as glucose, fructose, and sucrose, are converted into cellular energy and thereby producing ethanol, and carbon dioxide as metabolic waste products.

In an exemplary aspect, the gas producing organism is yeast or an ethanol producing bacteria. These organisms may carry out ethanol fermentation on sugars in the absence of oxygen. Because the process does not require oxygen, ethanol fermentation is classified as anaerobic. Ethanol fermentation is responsible for the rising of bread dough, the production of ethanol in alcoholic beverages, and for much of the production of ethanol for use as fuel.

A number of yeast strains known to be able to ferment sugars by those skilled in the art may be used. Suitable yeasts include those of the genera *Saccharomyces* and *Kluyveromyces, Pachysolen tannopholus*, and *Candida* lusitaniae. In preferred embodiments, *Saccharomyces cerevisiae, Saccharomyces bayanus* and mixtures thereof may be utilized.

Additionally, a number of bacteria strains may be used that are known to be able to ferment sugars by those skilled in the art. For example, any *zymomonas* that are capable of converting a fermentable carbohydrate to ethanol can be used in the present invention. Useful bacteria include those currently classified taxonomically as *zymomonas mobilis* and *zymomonas anaerobia*.

In one example, fruit juices, such as grape juice, and a yeast culture are added to a container to produce a sparkling wine. The process of fermentation in wine is the catalyst function that turns the glucose in grape juice into an alcoholic beverage. During fermentation, yeast interacts with sugars in the juice to create ethanol and carbon dioxide.

Surfactants may be added to the wine and sealed in a container that may provide a personal care cleaning product. The yeast is allowed to continue to react with the sugars in the juice to further pressurize the composition and provide the carbonated gas in the composition in situ. In this exemplary composition, careful selection of the surfactant by an individual skilled in the art is necessary to help prevent the surfactant composition from prohibiting the yeast from interacting with the sugars.

For example, the at least one surfactant in the gas pressurized liquid composition is a nonionic surfactant. Use of nonionic surfactants allows for a surfactant to be included in the composition while not killing or otherwise inactivating the gas producing yeast or bacteria. Surprisingly, as a result, production of a gas in the composition may be produced in situ. By doing so, the aqueous composition is maintained in a pressurized state and produces gas until the composition is used or all of the fermentable carbohydrate is consumed. A single nonionic surfactant may be used, or several nonionic surfactants may be used in combination. Typically, the gas pressurized liquid composition comprises a surfactant in an amount of from about 0.01 wt. % to about 60 wt. %, more preferably about 0.05 wt. % to about 50 wt. %. Examples of nonionic surfactants are found below.

Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_{8-18}$) acids, condensation products of ethylene oxide with long chain amines or amides, condensation products of ethylene oxide with alcohols, and mixtures thereof.

Suitable nonionic surfactants may include, for instance, alkyl polysaccharides, alcohol ethoxylates, block copolymers, castor oil ethoxylates, ceto-oleyl alcohol ethoxylates, cetearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, mono-branched alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, tallow oil fatty acid ethoxylates, tallow amine ethoxylates, tridecanol ethoxylates, acetylenic diols, polyoxyethylene sorbitols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_{6-22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, poloxamers such as poloxamer 188, polysorbate 21, polysorbate 40, polysorbate 60, polysorbate 61, polysorbate 65, polysorbate 80, polysorbate 81, polysorbate 85, sorbitan caprylate, sorbitan cocoate, sorbitan diisostearate, sorbitan dioleate, sorbitan distearate, sorbitan fatty acid ester, sorbitan isostearate, sorbitan laurate, sorbitan oleate, sorbitan palmitate, sorbitan sesquiisostearate, sorbitan sesquioleate, sorbitan sesquistearate, sorbitan stearate, sorbitan triisostearate, sorbitan trioleate, sorbitan tristearate, sorbitan undecylenate, or mixtures thereof. Commercially available nonionic surfactants may include the SURFYNOL® range of acetylenic diol surfactants available from Air Products and Chemicals of Allentown, Pa.; the TWEEN® range of polyoxyethylene surfactants available from Fisher Scientific of Pittsburgh, Pa.; and the TRITON® range of polyoxyethylene surfactants (e.g., TRITON® X-100, polyoxyethylene-10 isooctylcyclohexyl ether) available from Sigma-Aldrich Chemical Co. of St. Louis, Mo.

Alkyl glycoside nonionic surfactants may also be employed and are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543, which are incorporated herein in their entirety by reference thereto for all purposes, describe alkyl glycosides and/or methods for their preparation. Suitable examples are commercially available under the names of Glucopon™ 220, 225, 425, 600 and 625, PLANTACARE®, and PLANTAPON®, all of which are available from Cognis Corp. of Ambler, Pa. These products are mixtures of alkyl mono- and oligoglucopyranosides with alkyl groups based on fatty alcohols derived from coconut and/or palm kernel oil. Glucopon™ 220, 225 and 425 are examples of particularly suitable alkyl polyglycosides. Glucopon™ 220 is an alkyl polyglycoside that contains an average of 1.4 glucosyl residues per molecule and a mixture of 8 and 10 carbon alkyl groups (average carbons per alkyl chain 9.1). Glucopon™ 225 is a related alkyl polyglycoside with linear alkyl groups having 8 or 10 carbon atoms (average alkyl chain 9.1 carbon atoms) in the alkyl chain. Glucopon™ 425 includes a mixture of alkyl polyglycosides that individually include an alkyl group with 8, 10, 12, 14 or 16 carbon atoms (average alkyl chain 10.3 carbon atoms). Glucopon™ 600 includes a mixture of alkyl polyglycosides that individually include an alkyl group with 12, 14 or 16 carbon atoms (average alkyl chain 12.8 carbon atoms). Glucopon™ 625 includes a mixture of alkyl polyglycosides that individually include an alkyl group having 12, 14 or 18 carbon atoms (average alkyl chain 12.8 carbon atoms). Still other suitable alkyl glycosides are available from Dow Chemical Co. of Midland, Mich. under the Triton™ designation, e.g., Triton™ CG-110 and BG-10.

Other useful nonionic surfactants include water soluble silicones such as PEG-10 Dimethicone, PEG-12 Dimethicone, PEG-14 Dimethicone, PEG-17 Dimethicone, PPG-12 Dimethicone, PPG-17 Dimethicone and derivatized/functionalized forms thereof such as Bis-PEG/PPG-20/20 Dimethicone Bis-PEG/PPG-16/16 PEG/PPG-16/16 Dimethicone, PEG/PPG-14/4 Dimethicone, PEG/PPG-20/20 Dimethicone, PEG/PPG-20/23 Dimethicone, and Perfluorononylethyl Carboxydecyl PEG-10 Dimethicone.

In another exemplary aspect of the present disclosure, a product and method for storing and delivering a personal care cleansing composition is disclosed. The personal care cleansing composition is an aqueous composition having at least one surfactant wherein the aqueous composition is a gas pressurized liquid is also disclosed. In one aspect, the composition is stored in an internal reservoir in a container such that when a sealing device is removed from the opening, the composition foams and plumes out the opening of the container. The overall degree of foam and plume which evacuates the pressurized container may vary substantially depending on the application of interest.

Referring now to the FIG. 1, the personal care cleansing product 10 comprises a container 12 having a pressurized internal reservoir 14 in communication with an opening 16 in the container 12. Stored in the container 12 is a composition 20 for utilization as a soap or cleansing product. The internal reservoir 14 in the container 12 must be able to hold a low viscosity liquid that is stored in a pressurized state and withstand the elevated pressure.

A sealing device 22 maintains the composition 20 in a pressured state in the internal reservoir 14 of the container 12. In one aspect, the aqueous composition 20 comprises a gas and is stored in a pressured state inside the internal reservoir 14 with a valveless opening 16 that allows the composition 20 to independently propel itself out from the opening 16 of the container 12. As such, consumers and users of the product 10 will further enjoy opening and utilizing the composition 20 inside the container 12.

The container 12 also provides a method of opening that allows for the quick release of pressure from the internal reservoir to generate foam or bubbles in the composition. The method of storing and delivering the personal care cleansing product of the present disclosure involves providing a valveless container having an opening and a sealing device 22 and storing an aqueous composition under high pressure in an inner reservoir. As illustrated in FIG. 2, since the aqueous composition includes at least one surfactant and is carbonated or gassed in the internal reservoir 14 of the container 12, removing the sealing device 22 from the opening 16 of the container 12 releases the pressurized gas from the composition 20 causing the composition 20 to foam and the composition 20 to plume from the opening 16 of the container 12. There is no additional mechanical means necessary to cause the pressurized gas composition 20 to foam and plume from the container 12. A user of the product 10 will then pour the remainder of the composition from the container 12.

Alternatively, a consumer could shake the container prior to use. By shaking the container, the gas pressurized liquid composition will produce more bubbles and create higher pressure in the container. As a result, when the consumer opens the container, there is much quicker release of the pressurized gas causing more foam and more intense pluming and a significantly more pleasing experience of using the product by the consumer.

The personal care product of the present disclosure could include several sealing devices that would allow for a quick release of the composition from the pressurized container when the sealing device is removed from the opening of the container. For example, the sealing device for the opening of the container could include, but not be limited to, a pop-top utilized in aluminum cans, a cork or bottle stopper utilized in corked bottles, and frangible seals. For example, the container provided may be a bottle and the sealing device may be a cork. As the sealing device is removed, the pressurized composition bubbles and plumes out of the container. The overall degree of foam and plume which evacuates the pressurized container may vary substantially depending on the application of interest.

In another aspect of the present disclosure, the personal care cleansing composition provides excellent foam producing ability and foam persistence, is readily dispersed in bath water, and imparts moistness to the skin after bathing. The cleansing composition may be in any form known in the art, such as, for example, hand soaps, body soaps, body washes, shampoos, surface cleaners, dish soaps, facial cleansers, hand washes, and the like. These types of cleansing compositions typically include at least one foaming agent, such as a surfactant. Although discussed herein primarily in terms of a surfactant, it should be understood that the cleansing compositions of the present disclosure may comprise other cleansing agents, and need not comprise a surfactant.

For example, in certain embodiments, the compositions may comprise a thickener, a foaming agent (which may or may not comprise a surfactant), and optionally a solvent or other carrier. Examples of such compositions include, for example, hand sanitizers, lotions, anti-microbial compositions, and the like.

To produce the gas pressurized liquid composition within the container, the gas pressurized liquid composition may contain a fermentation base and at least one surfactant as described above. In one preferred example, the pressurized gas is produced by the fermentation of a fruit juice to produce carbon dioxide and providing a sparkling wine. By providing a sparkling wine as the aqueous fermentation base gives the personal care cleansing product the odor and consistency of champagne or wine that will also improve the experience of using the product for a consumer.

In another example, pressurizing gas into the composition may involve injecting the aqueous composition with an acceptable pressurized gas and bottling the formulation under high pressure. The gas will dissolve in the liquid and be maintained under high pressure until the container is opened, thus releasing the gas and causing the escaping gas to form foam in the surfactant solution much like a shaken-up soda can or a freshly uncorked bottle of champagne. Acceptable gases utilized to pressurize the composition in the container include, but are not limited to, air, carbon dioxide, nitrogen, nitric oxide, isobutene and other suitable inert carriers, as well as other gases that generate sufficient pressure within the container.

In this alternative embodiment with injected gas, the pressurized gas liquid composition preferably contains one or more surfactants selected from anionic, nonionic, cationic, amphoteric and zwitterionic surfactants and mixtures thereof. Typically, the personal care cleansing product comprises a surfactant in an amount of from about 0.01 wt. % to about 60 wt. %, more preferably about 0.05 wt. % to about 50 wt. %. The surfactant is included in the cleansing composition to provide a cleaning, lathering, and/or foaming action.

Where present, amphoteric and zwitteronic surfactants are generally used in combination with one or more anionic and/or nonionic surfactants. For example, the cleansing composition may include at least one surfactant that is a mixture of amphoteric and anionic surfactants. One preferred mixture may include an anionic surfactant, sodium lauryl sulfate, and an amphoteric surfactant of cocamidopropyl betaine.

In addition to nonionic surfactants, the cleansing composition may also contain other types of surfactants. In particular, the surfactant could include surfactants in classes such as anionic, cationic, amphoteric and/or zwitterionic surfactants.

Exemplary anionic surfactants include alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkylauryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, or mixtures thereof. Particular examples of anionic surfactants include, but are not limited to, $C_{8-22}$ alkyl sulfates, $C_{8-22}$ fatty acid salts, $C_{8-22}$ alkyl ether sulfates having one or two moles of ethoxylation, $C_{8-22}$ alkyl ether phosphates having one to three moles of ethoxylation, $C_{8-22}$ alkoyl sarcosinates, $C_{8-22}$ sulfoacetates, $C_{8-22}$ sulfosuccinates, $C_{8-22}$ alkyl diphenyl oxide disulfonates, $C_{8-22}$ alkyl carbonates, $C_{8-22}$ alpha-olefin sulfonates, methyl ester sulfonates, and blends thereof. The $C_{8-22}$ alkyl group may be a straight chain (e.g., lauryl) or branched (e.g., 2-ethylhexyl). The cation of the anionic surfactant may be an alkali metal (e.g., sodium or potassium), ammonium, $C_{1-4}$ alkylammonium (e.g., mono-, di-, tri-), or $C_{1-3}$ alkanolammonium (e.g., mono-, di-, tri). More specifically, such anionic surfactants may include, but are not limited to, lauryl sulfates, octyl sulfates, 2-ethylhexyl sulfates, potassium laureth phosphate, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, cetyl sulfates, and similar surfactants.

Amphoteric and zwitterionic surfactants may also be employed, wherein at least one of the aliphatic substituents contains from about 8 to 22 carbon atoms and at least one of the aliphatic substituents contains an anionic water-solubilizing group, such as a carboxy, sulfonate, or sulfate group. Some examples of amphoteric surfactants include, but are not limited to, betaines, alkylamido betaines, sulfobetaines, N-alkyl betaines, sultaines, amphoacetates, amophodiacetates, imidazoline carboxylates, sarcosinates, acylamphoglycinates, such as cocamphocarboxyglycinates and acylamphopropionates, and combinations thereof. Additional classes of amphoteric surfactants include phosphobetaines and the phosphitaines. For instance, some examples of such amphoteric surfactants include, but are not limited to cocamidopropyl betaine, lauramidopropyl betaine, meadowfoamamidopropyl betaine, sodium cocoyl sarcosinate, sodium cocamphoacetate, disodium cocoamphodiacetate, ammonium cocoyl sarcosinate, sodium cocoamphopropionate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof. Suitable zwitterionic surfactants include, for example, alkyl amine oxides, silicone amine oxides, and combinations thereof. Specific examples of suitable zwitterionic surfactants include, for example, 4-[N,N-di(2-hydroxyethyl)-N-octadecylammonio]-butane-1-carboxylate, S—[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydorxy-pentane-1-sulfate, and combinations thereof.

Cationic surfactants may also be employed in the present invention, such as quaternized amine ethoxylates, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include behentrimonium chloride, stearalkonium chloride, distearalkonium chloride, chlorhexidine digluconate, polyhexamethylene biguanide (PHMB), polyaminopropyl biguanide, cetylpyridinium chloride, benzammonium chloride, benzalkonium chloride, and combinations thereof.

Additional ingredients may also be added to the surfactant solution to promote an additional end benefit. For example, moisturizing ingredients to provide a moisturizing benefit to the skin would be a beneficial addition to the self foaming composition of the present disclosure. When included, the moisturizing ingredient moisturizes the skin and/or provides a barrier to minimize loss of moisture from the skin.

Some examples of moisturizing ingredients that could be included in the self foaming composition of the present disclosure include, for example, glycerin, glycols, and sorbitol; synthetic oils such as mineral oil and petrolatum; natural oils such as sunflower oil, jojoba oil, and safflower oil; silicones such as dimethicone, cyclomethicone; esters such as isopropyl palmitate, caprylic/capric triglyceride; butters such as cocoa butter, coffee butter, and shea butter; and barrier ingredients such as fatty acids, fatty alcohols, and waxes.

Soothing ingredients are another component that are often used in bath products to reduce skin irritation from rashes and sensitive skin. Soothing ingredients that may be added to the composition could include but not be limited to: SymCalmin from Symrise, oat derived ingredients such as colloidal oatmeal, bisabolol, allantoin, herbal extracts such as chamomile extract and the like.

The composition of the present disclosure may additionally include adjunct ingredients conventionally found in cleansing compositions in their art-established fashion and at their art-established levels. For example, the compositions may comprise additional compatible active materials for combination therapy, such as additional antimicrobial agents, antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof. Other suitable additives that may be included in the compositions of the present disclosure include colorants, deodorants, fragrances, perfumes, emulsifiers, anti-foaming agents, lubricants, humectants, skin conditioning agents, skin protectants and skin benefit agents (e.g., aloe vera and laponite), solvents, solubilizing agents, suspending agents, wetting agents, preservatives, pH adjusting ingredients, chelators, propellants, dyes and/or pigments, and combinations thereof. Further examples of suitable ingredients include those described in CTFA, International Cosmetic Ingredient Dictionary and Handbook, 12th Ed. (2008).

The cleansing product may also comprise a thickener, which acts to thicken or increase the viscosity of the cleansing composition. Typically, the composition will comprise from about 0.01 wt. % to about 5 wt. % of thickener.

A variety of thickeners may be used in the cleansing compositions described herein. In one embodiment, the thickener may be a cellulosic thickener or gum. Examples of suitable cellulosic or gum thickeners include xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, hydroxypropylcellulose, hydroyethylcellulose, propylene glycol alginate, hydroxypropyl guar, amylopectin, cellulose gum, hydroxypropyl methylcellulose, microcrystalline cellulose, dehydroxanthan gum, and dehydroxanthan gum. Additional examples of suitable thickeners include but are not limited to silica, fumed silica, chitosan, modified chitosan, colloidal silica, non-acrylic based carbomers as well as combinations of the aforementioned thickeners. When the thickener is a cellulosic or gum thickener, the thickener is preferably present in the cleansing composition in an amount of from about 0.01 wt. % to about 2 wt. %, and more preferably in an amount of from about 0.1 wt. % to about 1 wt. %.

The present disclosure is illustrated by the following examples which are merely for the purpose of illustration and are not to be regarded as limiting the scope of the disclosure or manner in which it may be practiced.

Example 1

In this example, a personal care cleansing product is produced for use in accordance with the present disclosure. Specifically, a plastic carboy capable of holding 2 gallons of liquid was used to prepare a base composition with carbonated gas. The base composition was produced by adding 500 mL of a grape juice concentrate, 15 grams of dextrose, and the remaining balance with water. The composition was mixed until the concentrate was diluted and the sugar was completely dissolved. Approximately, 10 mL of *Saccharomyces cerevisiae* culture and 10 mL of the *Saccharomyces bayanus* culture were added to the diluted and sweetened juice composition. The carboy was gently shaken to mix the yeast into the wine starter. The carboy was then sealed with the gas lock mechanism that prevents exterior gas from entering the carboy but allows carbon dioxide to escape. The composition was then allowed to ferment at room temperature for four weeks. At this time, an additional 5 grams of dextrose was added to ensure the yeast had enough nutrients to ferment for an additional 2 weeks. The fermentation process produced carbonated gas in the base composition. Then, approximately 24 grams of glucose were added to 1 Liter of the base composition and mixed.

Subsequently, a champagne bottle with a volume of 187 mL was provided and filled with the base composition. Approximately 18 grams of poloxamer 188 (polyethylene-polyproylene glycol) was added as a surfactant. The base composition was then added and the bottle was corked with a plastic stopper and secured with champagne wires (wire netting commonly associated with champagne bottles for maintaining the stopper in the bottle). The bottles were inverted to mix surfactant into the base composition. The subsequent gas pressurized liquid composition was allowed to ferment at room temperature for one month. The gas pressurized liquid composition is illustrated in Table 1 below.

TABLE 1

Example gas pressurized liquid composition 1

| Component | Wt. % | Grams |
|---|---|---|
| Base Composition | 90.0 | 162 |
| Poloxamer 188 | 10.0 | 18 |

After one month, the gas pressurized liquid composition appears clear with a small amount of yeast sediment in the bottom of the bottle. Upon opening, the bottle pops similar to a bottle of champagne and the gas pressurized liquid composition bubbles over the top of the bottle. The composition was then added to a beaker of water and the composition created bubbles like a bubble bath.

Example 2

A base composition was prepared as described above with reference to Example 1. Subsequently, two champagne bottles were provided and filled with the base composition. Approximately, 36 grams of polysorbate 20 was added as a surfactant to both bottles. The bottles were corked with plastic stoppers and secured with champagne wires. The bottles were inverted to mix surfactant into the base composition. The subsequent gas pressurized liquid composition was allowed to ferment at room temperature for one month. The exemplary gas pressurized liquid composition is illustrated in Table 2 below.

TABLE 2

Example gas pressurized liquid composition 2

| Component | Wt. % | Grams |
|---|---|---|
| Base Composition | 80.0 | 144 |
| Polysorbate 20 | 20.0 | 36 |

After one month, the gas pressurized liquid composition was clear with a small amount of yeast sediment in the bottom of the bottles. The bottles were opened and "popped" like champagne. The gas pressurized liquid composition bubbled over the top of the bottles. The composition behaved like a bubble bath when added to water. The bubbles created were stable and maintained their form for a long enough period of time to persist for a consumer to take a bath.

Example 3

A base composition was prepared as described above with reference to Example 1. Subsequently, two champagne bottles were provided and filled with base composition. Approximately, 36 grams of decyl glucoside was added as a surfactant. The bottles were corked with plastic stoppers and secured with champagne wires. The bottles were inverted to mix surfactant into the base composition. The subsequent gas pressurized liquid composition was allowed to ferment at room temperature for one month. The gas pressurized liquid composition is illustrated in Table 2 below.

TABLE 3

Example gas pressurized liquid composition 3

| Component | Wt. % | Grams |
|---|---|---|
| Base Composition | 80.0 | 144 |
| Decyl glucoside | 20.0 | 36 |

After one month, the gas pressurized liquid composition was clear with a small amount of yeast sediment in the bottom of the bottles. The bottles were opened, popped like champagne and the gas pressurized liquid composition bubbled over the top of the bottles. Copious amounts of bubbles were maintained in the bottle. The composition behaved like a bubble bath when added to water. The bubbles created in the water were stable and long lasting.

Having described the disclosure in detail, it will be apparent that modifications and variations are possible without departing from the scope of the disclosure defined in the appended claims.

The invention claimed is:
1. A self-gassing liquid cleansing composition comprising:
    an aqueous fermentation base comprising effective amounts of at least one fermentable carbohydrate and at least one viable gas producing organism; and
    at least one surfactant; wherein the surfactant is present from about 10% to about 60% based on the total weight of the composition.
2. The self-gassing liquid cleansing composition of claim 1 wherein the at least one fermentable carbohydrate is selected from glucose, fructose, sucrose and/or combinations thereof.
3. The self-gassing liquid cleansing composition of claim 2 wherein the at least one fermentable carbohydrate is a sugar from a fruit juice.
4. The self-gassing liquid cleansing composition of claim 1 wherein the at least one gas producing organism is selected from yeast and/or an ethanol producing bacteria.
5. The self-gassing liquid cleansing composition of claim 1 wherein the at least one surfactant is a nonionic surfactant, wherein the nonionic surfactant does not kill the viable gas producing organism.
6. The self-gassing liquid cleansing composition of claim 1 wherein the surfactant is nonionic and is selected from methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_{6-22}$) alcohol, including 3 to 20 ethylene oxide moieties, polyoxyethylene-20 isohexadecyl ether, polyoxyethylene-23 glycerol laurate, PEG-80 sorbitan laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG-600 dioleate, PEG-400 dioleate, decyl glucoside, poloxamers, polysorbate 21, polysorbate 40, polysorbate 60, polysorbate 61, polysorbate 65, polysorbate 80, polysorbate 81, polysorbate 85, sorbitan caprylate, sorbitan cocoate, sorbitan diisostearate, sorbitan dioleate, sorbitan distearate, sorbitan fatty acid ester, sorbitan isostearate, sorbitan laurate, sorbitan oleate, sorbitan palmitate, sorbitan sesquiisostearate, sorbitan sesquioleate, sorbitan sesquistearate, sorbitan stearate, sorbitan triisostearate, sorbitan trioleate, sorbitan tristearate, sorbitan undecylenate, PEG-10 Dimethicone, PEG-12 Dimethicone, PEG-14 Dimethicone, PEG-17 Dimethicone, PPG-12 Dimethicone, PPG-17 Dimethicone and derivatized/functionalized forms thereof selected from Bis-PEG/PPG-20/20 Dimethicone, Bis-PEG/PPG-16/16 PEG/PPG-16/16 Dimethicone, PEG/PPG-14/4 Dimethicone, PEG/PPG-20/20 Dimethicone, PEG/PPG-20/23 Dimethicone, Perfluorononylethyl Carboxydecyl PEG-10 Dimethicone and/or mixtures thereof.

7. A method of storing and delivering a personal care cleansing product comprising:
provide a valveless container having an opening and a sealing device;
storing the self-gassing liquid cleansing composition of claim 1 therein; and
removing the sealing device from the opening and allowing the composition to foam and plume out the opening of the container.

8. The method of claim 7 wherein the surfactant is present from about 10% to about 50% based on the total weight of the composition.

9. The method of claim 7 wherein the at least one surfactant is a nonionic surfactant, and wherein the nonionic surfactant does not kill the viable gas producing organism.

10. The method of claim 7 wherein pressurized gas is further injected into the composition and stored under high pressure.

11. The method of claim 10 wherein the pressurized gas is selected from carbon dioxide, nitrogen, nitric oxide, isobutene and other suitable inert carriers.

12. The method of claim 7 wherein the at least one surfactant is selected from anionic, nonionic, cationic, amphoteric, zwitterionic surfactants and mixtures thereof.

13. The method of claim 12 wherein the at least one surfactant is a mixture of amphoteric and anionic surfactant.

14. The method of claim 12 wherein the anionic surfactant is sodium lauryl sulfate and the amphoteric surfactant is cocamidopropyl betaine.

15. The method of claim 7 wherein the sealing device is a pop-top utilized in aluminum cans, a bottle stopper utilized in corked bottles and frangible seals.

16. The method product of claim 7 wherein the container provided is a bottle and the sealing device is a bottle stopper.

17. The method in claim 7 wherein the composition further comprises an ingredient selected from the group consisting of emollients, humectants, natural fats and oils, anti-irritants, antimicrobial agents, antioxidants, anti-parasitic agents, anti-pruritics, antifungals, antiseptic actives, keratolytic actives, anti-stinging agents, anti-reddening agents, astringents, biological actives, deodorants, external analgesics, film formers, fragrances, skin condition agents, skin exfoliating agents, skin protectants, skin soothing ingredients, sunscreens and combinations thereof.

18. A personal care cleansing product comprising:
a valveless container having a pressurized internal reservoir, an opening and a sealing device positioned in the opening;
the self-gassing liquid cleansing composition of claim 1 therein, the composition stored in the container such that when the sealing device is removed from the opening, the composition foams and plumes out the opening of the container.

19. The personal care cleansing product of claim 18 wherein pressurized gas is produced by fermentation of a fruit juice to produce carbon dioxide in the composition.

20. The personal care cleansing product of claim 18 wherein the surfactant is a nonionic surfactant.

21. The personal care cleansing product of claim 18 wherein the at least one surfactant is selected from anionic, nonionic, cationic, amphoteric, zwitterionic surfactants and mixtures thereof.

22. The personal care cleansing product of claim 18 wherein the container is a bottle and the sealing device is a bottle stopper.

23. The personal care cleansing product of claim 18 wherein pressurized gas is further injected into the composition and the composition is bottled under high pressure.

* * * * *